United States Patent
Yuen et al.

(10) Patent No.: US 9,354,167 B2
(45) Date of Patent: May 31, 2016

(54) METHOD AND APPARATUS FOR MEASURING APPEARANCE AND DISAPPEARANCE TEMPERATURES OF WAX FOR TRANSPARENT, TRANSLUCENT AND OPAQUE OILS

(71) Applicants: Vivian Hoi Nga Yuen, Vancouver (CA); Edmund K H Woo, Richmond (CA); Gordon S Y Chiu, Richmond (CA)

(72) Inventors: Vivian Hoi Nga Yuen, Vancouver (CA); Edmund K H Woo, Richmond (CA); Gordon S Y Chiu, Richmond (CA)

(73) Assignee: Phase Technology, Richmond, BC (CA)

( * ) Notice: Subject to any disclaimer, the term of this patent is extended or adjusted under 35 U.S.C. 154(b) by 0 days.

(21) Appl. No.: 14/507,979

(22) Filed: Oct. 7, 2014

(65) Prior Publication Data

US 2016/0097717 A1    Apr. 7, 2016

(51) Int. Cl.
*G01N 21/00* (2006.01)
*G01N 21/51* (2006.01)
*G01N 21/03* (2006.01)
*G01N 21/84* (2006.01)

(52) U.S. Cl.
CPC ............ *G01N 21/51* (2013.01); *G01N 21/0332* (2013.01); *G01N 21/84* (2013.01); *G01N 2021/513* (2013.01); *G01N 2201/0231* (2013.01); *G01N 2201/0233* (2013.01)

(58) Field of Classification Search
CPC ... G01N 21/51; G01N 21/0332; G01N 21/84; G01N 2021/513; G01N 2201/0231; G01N 2201/0233
See application file for complete search history.

(56) References Cited

U.S. PATENT DOCUMENTS

| | | | | |
|---|---|---|---|---|
| 4,193,692 A * | 3/1980 | Wynn | ...................... | G01N 21/51 356/341 |
| 4,893,558 A * | 1/1990 | Gouch | ................. | B65H 23/046 101/211 |
| 5,007,733 A * | 4/1991 | Laurent | .............. | G01N 33/2811 356/338 |
| 5,088,833 A * | 2/1992 | Tsang | ................. | G01N 33/2811 374/17 |
| 5,641,230 A * | 6/1997 | Okubo | .................... | G01N 25/68 356/339 |
| 2006/0139632 A1* | 6/2006 | Gerner | ................... | G01N 21/05 356/246 |
| 2006/0263256 A1* | 11/2006 | Koshel | ...................... | C23C 8/06 422/83 |
| 2007/0024459 A1* | 2/2007 | Cole | ..................... | G01F 1/6842 340/630 |
| 2007/0276169 A1* | 11/2007 | Tohidi | .................. | G01N 33/225 585/15 |
| 2007/0287881 A1* | 12/2007 | Akimov | ................ | A61M 21/00 600/26 |
| 2012/0044968 A1* | 2/2012 | Haran | ................ | G01N 33/2811 374/17 |
| 2012/0176615 A1* | 7/2012 | Brown | .................. | G01J 3/2803 356/328 |
| 2014/0016130 A1* | 1/2014 | Badiei | ...................... | F23N 5/02 356/342 |

\* cited by examiner

*Primary Examiner* — Kara E Geisel
*Assistant Examiner* — Hina F Ayub
(74) *Attorney, Agent, or Firm* — John J. Elnitski, Jr.

(57) ABSTRACT

An apparatus and method for the measurement of wax appearance temperature and wax disappearance temperature. The apparatus includes the following. The sample receptacle having a receptacle opening, including a bottom, at least one side and an open top. The sample receptacle including an inlet and an outlet for sample insertion and removal. The at least one side about the receptacle opening being light absorbing. The sample receptacle including a transparent cover mounted over the open top. The bottom of the receptacle opening having a reflective upper surface. A thermo device temperature change of the sample. A thermometer to register current temperature of the sample. A viewing chamber above the transparent cover, where the viewing chamber is surrounded by material that is light absorbing. A light emitting device to project light through the viewing chamber and the transparent cover.

21 Claims, 9 Drawing Sheets

METHOD AND APPARATUS FOR MEASURING APPEARANCE AND DISAPPEARANCE TEMPERATURES OF WAX FOR TRANSPARENT, TRANSLUCENT AND OPAQUE OILS

BACKGROUND

The present invention relates generally to apparatus and methods of detecting the appearance and disappearance of wax particles in oil, and more particularly to determining appearance and disappearance temperature of wax particles in transparent, translucent and opaque oils.

Wax appearance temperature (WAT), also known as cloud point (CP), and wax disappearance temperature (WDT) are of fundamental and pragmatic significance to the petroleum industry. As defined by the American Society of Testing and Materials (ASTM) standard test methods D2500, D3117 or D5773, WAT or CP is the temperature at which haziness caused by formation of small wax crystals is first observed in a sample of crude or refined oil under prescribed cooling conditions. In an analogous manner, WDT is the temperature at which cloudiness caused by these wax crystals re-dissolve into liquid form under specified warming conditions.

The measurement of WAT and WDT is important for crude oil, since environmental changes may lead to phase transition and solids formation during oil production, oil storage in containers or tankers, or oil transport through pipeline, railway or trucks. The presence of wax crystals in the oil may restrict flow or plug a fuel filter. Depending on the rate of wax deposition or melting, WAT or WDT may define the lower limit of acceptable operability of equipment or processes associated with oil. For example, wax problems in production wells are very costly because of production down time for wax removal. Any deposition in a pipeline will cause a reduction in flow rates, and it is expensive and time-consuming to clean. As oil companies move into arctic environments and deep-water area for oil production in order to meet increasing oil demand, preventing and mitigating wax deposits becomes increasingly important.

The measurement of CP or WAT by ASTM method D2500 is limited to fuels that are transparent in a minimum of 40 mm thickness, and with a CP below 49° C. The method's sensitivity depends on the amount and size of wax, and the subjective judgment of the operator. It is a time consuming method. In contrast, most crude oils are opaque visually before reaching 40 mm in thickness and some may have WAT warmer than 49° C. Therefore D2500 is not applicable for use with certain oils.

Cross Polarized Microscopy (CPM) is one of the techniques for WAT measurement. To determine WAT, a sample is to be preheated and transferred to a microscope slide. Two polarizers are used: the first one restricts the light to undulate in only one direction, while the second one is positioned at 90° from the first polarizer and completely blocks the light wave. Wax crystals on the slide are detected by rotating the polarization plane of the linearly polarized light. The sensitivity of CPM depends on the size of wax and film thickness, as well as scale of magnification. However, the restricted field view makes it difficult to detect the first crystal. CPM requires some microscopic wax crystals to form for a detectable signal. The CPM method requires experienced operator to prepare the microscopy slides, set up the microscope and detect the first wax crystals from the images. It is therefore not a practical method to use in a daily routine as an analytical tool for WAT measurement.

Differential Scanning Calorimetry (DSC) detects WAT by measuring the difference in heat absorbed or released between a reference sample and the test sample at a given cooling or warming rate. The reference needs to have known properties and be thermally inert (i.e. does not form wax) over the temperature range of measurement. The WAT is detected by a deviation of experimental data from the reference baseline and typically requires a significant amount of wax formation for sensible detection. Consequently it may be difficult to obtain a reliable baseline and to pinpoint the deviation from the baseline, especially when crystallization rate is low and signal noise overshadows thermal effects. Measured WAT tends to be lower than the actual temperature of initial wax formation and interpretation of WAT depends on the experience of the operator.

Another method for measuring WAT is viscometry, which measures gradual change of rheological properties as wax precipitates. WAT is estimated by plotting viscosity versus 1/temperature. The sensitivity of this method depends on the amount and size of wax. It can detect WAT only when the volume fraction of crystals is large enough for the viscosity to increase exponentially to create a large enough change in signal for detection.

Filter plugging is another technique for measuring WAT. It is based on the continuous monitoring of pressure drop across a filter, while the sample flows through a temperature-controlled flow loop. To minimize the shear stress at the filter, 0.5 µm size filters are commonly used together with low flow rates. This is because at a high flow rate, the shear stress produced by the flow will tend to reduce the particle size and thus increase the amount of crystals required to plug the filter. The method depends highly on the flow rate used and the detection of WAT requires a significant amount of crystals with size larger than 0.5 µm to form. Filter Plugging is therefore more a metric of when sufficiently number of larger particles are formed to impede the flow rather than a measure of when the first wax crystal appears.

WAT is also measured by Fourier Transform Infrared Spectroscopy (FT-IR), which detects the increase in energy scattering due to wax solidification. The operator has to identify the linear regions in wavenumber and to calculate the WAT by determining the intersection of two nonparallel lines generated during when temperatures are higher and lower than the calculated WAT. This makes it difficult to detect the WAT if wax formation is gradual and the deviation from parallelism is subtle. Similar to DSC, this method requires large amount of wax for detection, and the interpretation of WAT depends on the operator's experience. Such a method is described in U.S. Pat. No. 6,841,779 B1 issued on Jan. 11, 2005 to Roehner et al.

Nuclear magnetic resonance (NMR) is also used for measuring WAT. The NMR parameters such as relaxation times are related to the chemical and physical properties of the sample. The method is found to be problematic and ineffective for crude oils with low wax. Such method is described in U.S. Pat. No. 7,688,071 B2 issued on Mar. 30, 2010 to Cheng et al.

Light scattering has been found to be a sensitive method for measuring WAT. A lens is used to concentrate light scattering caused by crystals and is extremely sensitive to small amounts of scattered light caused by tiny crystals. Such method is described in U.S. Pat. No. 5,088,833 issued on Feb. 18, 1992 to Tsang et al and implemented into ASTM D5773. It is applicable to testing relatively transparent samples but not opaque ones due to high opacity coefficient for visible light.

Due to limitations of various prior art methods, it is therefore beneficial to have a simple to practice, highly sensitive and precise method for measuring WAT/WDT of relatively opaque samples that is free of subjective operator interpretation.

It is an object of the present invention to provide apparatus and method of measuring WAT/WDT of relatively opaque samples of oil, while eliminating subjective operator interpretation.

SUMMARY OF THE INVENTION

An apparatus and method for the measurement of wax appearance temperature and wax disappearance temperature. The apparatus includes the following. The sample receptacle having a receptacle opening, including a bottom, at least one side and an open top. The sample receptacle including an inlet and an outlet for sample insertion and removal. The at least one side about the receptacle opening being light absorbing. The sample receptacle including a transparent cover mounted over the open top. The bottom of the receptacle opening having a reflective upper surface. A thermo device temperature change of the sample. A thermometer to register current temperature of the sample. A viewing chamber above the transparent cover, where the viewing chamber is surrounded by material that is light absorbing. A light emitting device to project light through the viewing chamber and the transparent cover.

DETAILED DESCRIPTION

The present invention provides both a method and apparatus primarily intended for the measurement of wax appearance temperature and wax disappearance temperature. The present invention is also suitable for measuring the temperature at which any light scattering phase forms or disappears in a transparent, translucent or opaque non-light scattering liquid when it is heated or cooled. Such phase may be a solid, an immiscible liquid or a gas. Therefore the present invention can be used for measuring the temperature of transitions between miscible and immiscible liquids, and transitions between a solid and liquid at melting or solidification.

The apparatus of the present invention measures the temperature at which a transition occurs between a transparent, translucent or opaque non-light scattering liquid and a light scattering phase. The apparatus includes a generally light proof chamber having light absorbing internal surfaces and has a gas inlet and gas outlet in the light proof chamber. The apparatus includes a liquid sample receiving receptacle within the light proof chamber. The liquid sample receiving receptacle has a bottom formed by a heat conductive material with an upper surface which is non-light scattering. The apparatus includes a removable transparent cover adapted to fit over the liquid sample receiving receptacle to allow light transmission. The apparatus includes the ability to keep a liquid sample surface flat without a meniscus and to control the sample thickness to a suitably thin layer. The apparatus includes an inlet port and an outlet port for the liquid sample receiving receptacle to allow the liquid sample and cleaning solvent to flow through the area between the liquid sample receiving receptacle and the transparent cover. The apparatus includes thermal contact with the bottom of the liquid sample receiving receptacle for changing the temperature of the bottom of the liquid sample receiving receptacle and temperature monitoring of the bottom of the liquid sample receiving receptacle. The apparatus includes a high power light beam source of near infrared (NIR) or infrared (IR) wavelength located to direct a beam of light onto the liquid sample at an incident angle so that light from the beam is largely reflected or absorbed by the upper surface of the liquid sample receiving receptacle. The apparatus includes scattered light detection arranged to detect light scattered by the liquid sample and changes in intensity of the scattered light. The scattered light detection is connected into a circuit capable of registering a change in light scattered from the liquid sample as the bottom of the liquid sample receiving receptacle is heated or cooled. The scattered light detection includes a lens which concentrates the light from the liquid sample onto a light detecting element.

Figure 1:
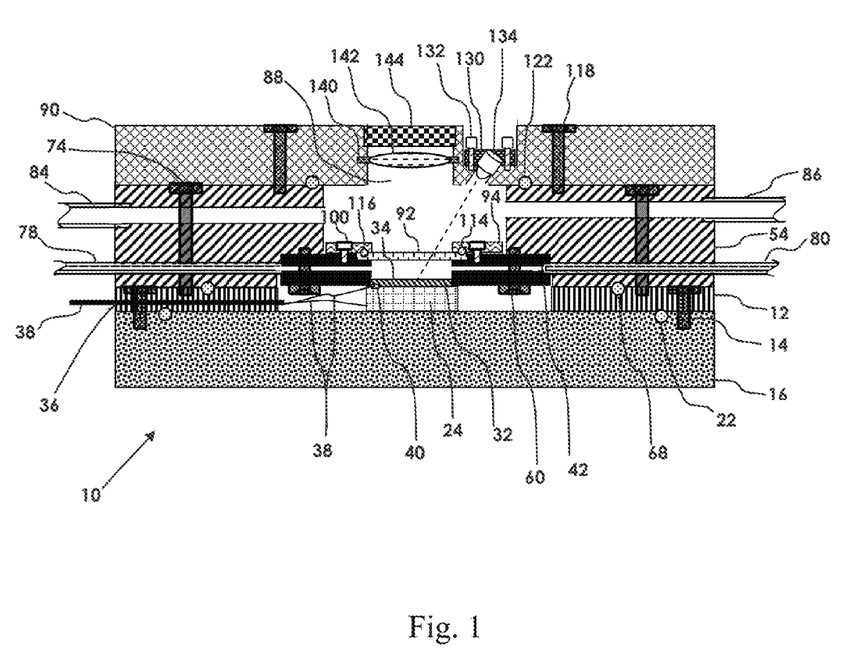
FIG. 1 is a side sectional view of an apparatus according to the present invention.
Figure 2:
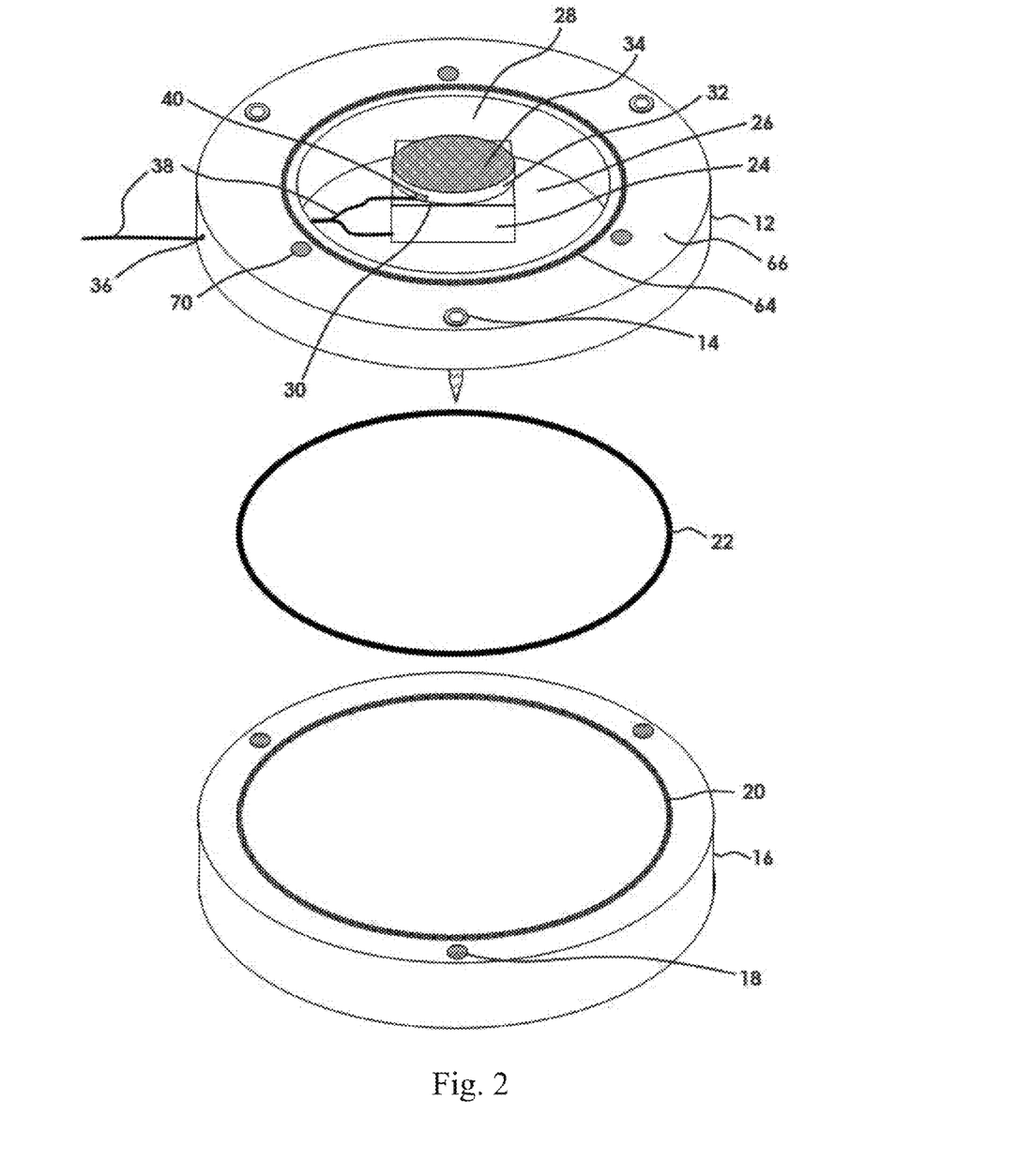
FIG. 2 is a perspective exploded view of components of the apparatus of FIG. 1 according to the present invention.

FIGS. 1-5 show a basic embodiment of the apparatus for wax appearance temperature measurement described above. FIG. 1 shows a sectional view of a wax appearance temperature measurement device 10 and FIG. 1 should be referred to during the description of the device 10. The device 10 includes a base 12 mounted by screws 14 onto a refrigerant cooled, metallic heat sink 16, as shown in FIG. 2. The heat sink 16 includes screw holes 18 and an O-ring groove 20. O-ring 22 rests in the O-ring groove 20 of the heat sink 16 to provide a seal between the heat sink 16 and the base 12. A thermo device shown as a thermoelectric device 24 is mounted to the heat sink 16 and is in contact with the heat sink 16 such that there is heat conductive contact between the thermoelectric device 24 and the heat sink 16. A peltier cooler is an example of a thermo device. The base 12 includes a center opening 26 to allow for the thermoelectric device 24 to project up from the heat sink 16. The thermoelectric device 24 spaced from the wall 28 of the center opening 26 of the base 12 such that the base 12 is thermally insulated from thermoelectric device 24. FIG. 2 shows a lower surface 30 of a receptacle bottom 32 attached to the top of the thermoelectric device 24, where the contact with each other is such that there is heat conductive contact between the thermoelectric device 24 and the lower surface 30 of the receptacle bottom 32. The receptacle bottom 32 is shown with an upper surface 34 of a polished flat mirror of about 10 mm diameter and preferably between 5 mm and 15 mm. The material of the receptacle bottom 32 should possess good thermal conductive property and able to be polished to form the upper surface 34 to reflect light of sufficiently good quality to form a meaningful image. Copper is found to satisfy both requirements of the receptacle bottom 32, but the upper surface 34 could also be chromed on the top surface of the copper in order to have good optical properties. The thermoelectric device 24 is capable of reducing the temperature of the receptacle bottom 32 to −25° C. or lower. The base 12 is provided with a side bore 36 for wires 38 which run both to the thermoelectric device 24 and to a platinum resistance thermometer 40 in contact with the lower surface 30 of the receptacle bottom 32.

Figure 3:
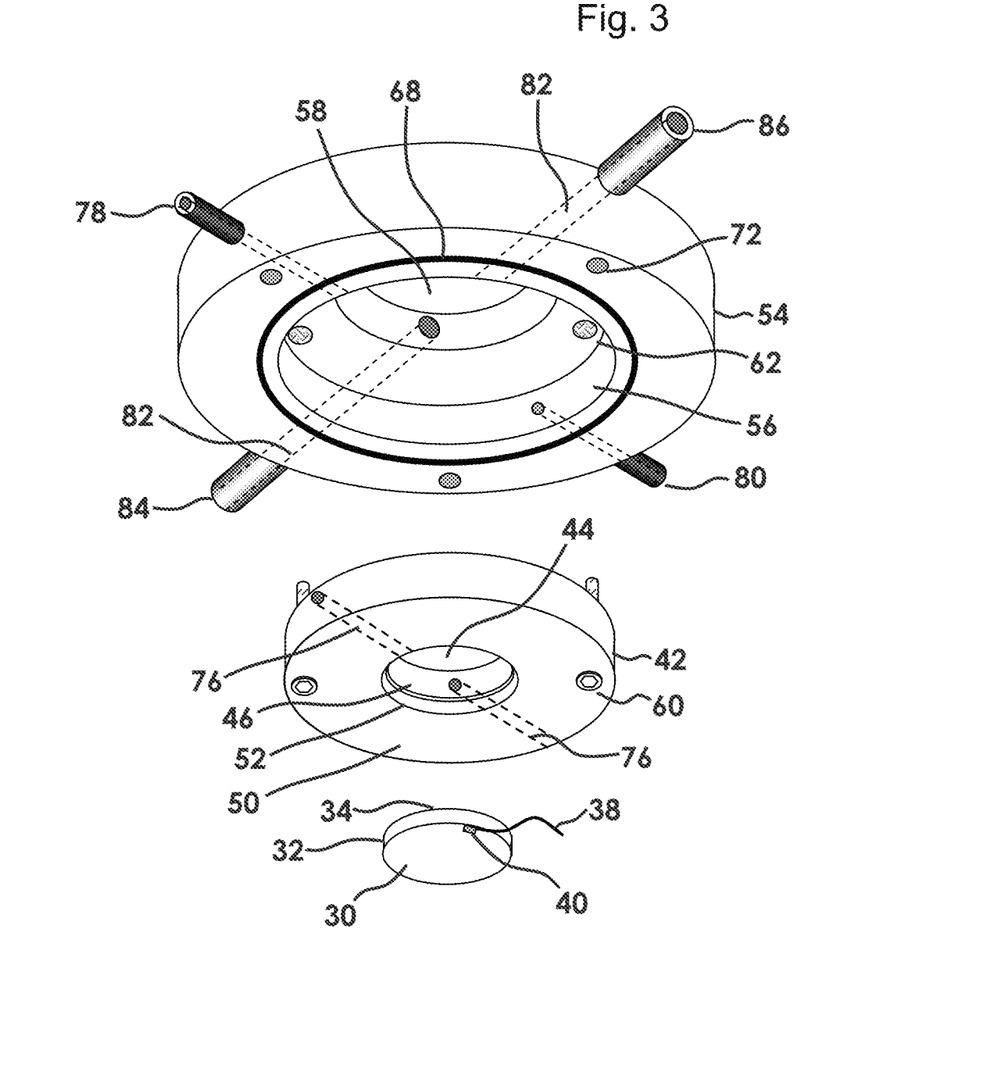
FIG. 3 is a perspective exploded view of components of the apparatus of FIG. 1 according to the present invention.

FIG. 3 shows a receptacle body 42 having a receptacle opening 44 to form the wall 46 of the receptacle. The receptacle body 42 is made of metal for thermal conductivity, for example aluminum may be used. The bottom 50 of the receptacle body 42 includes a counter-bore area 52 to receive the receptacle bottom 32. The receptacle bottom 32 fits snugly within the counter-bore area 52 so that a wall 46 of the receptacle opening 44 of the receptacle body 42 and upper surface 34 of the receptacle bottom 32 form the receptacle. A housing 54 includes a counter-bore opening 56 which leads to a smaller top opening 58. The receptacle body 42 is mounted into the counter-bore opening 56 of a housing 54 by screws 60 to screw holes 62 of the housing 54. The base 12 includes an O-ring groove 64 on an upper surface 66, as shown in FIG. 2. FIG. 3 shows an O-ring 68 that rests in the O-ring groove 64 of the base 12 to provide a seal between the base 12 and the housing 54. The base 12 includes screw holes 70 as shown in FIG. 2 and the housing 54 includes screw holes 72 as shown in FIG. 3 to receive screws 74 shown in FIG. 4 to secure the housing 54 to the base 12. The receptacle body 42 includes with two channels 76 which connect to a sample inlet tube 78 and sample outlet tube 80 which go through the housing 54. The housing 54 also includes purge ducts 82 connected to inlet tube 84 and outlet tube 86 so a viewing chamber 88 (FIG. 1) formed by the smaller top opening 58 of the housing 54 can be purged with a non-condensing gas.

Figure 4:
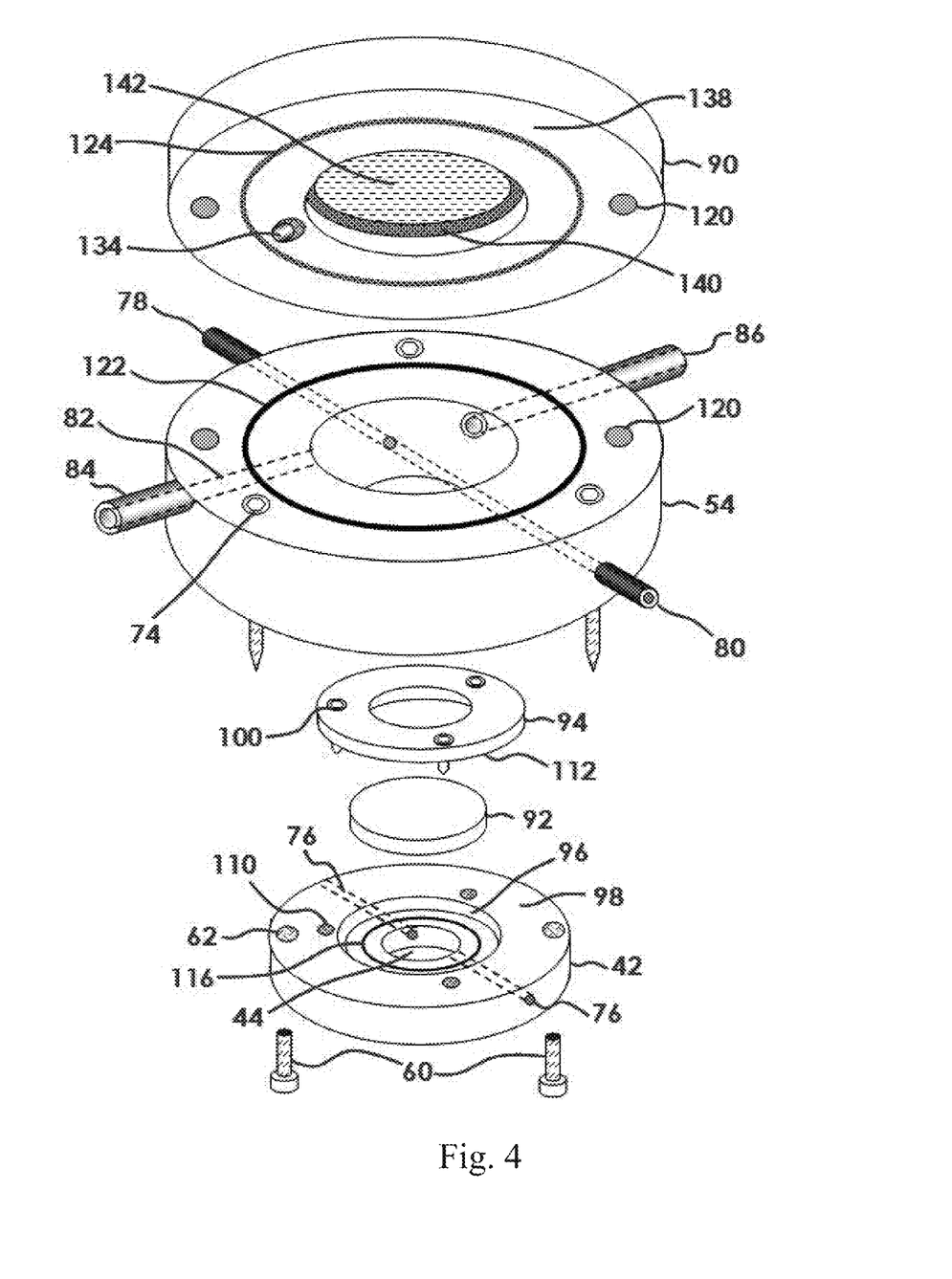
FIG. 4 is a perspective exploded view of components of the apparatus of FIG. 1 according to the present invention.

FIG. 4 shows the addition of a top 90, transparent cover 92 and cover holder 94. The receptacle body 42 includes a counter-bore 96 from an upper surface 98 of the receptacle body 42 to receive the transparent cover 92. The transparent cover 92 mounts into the counter-bore 96 of the upper surface 98 of the receptacle body 42 over the receptacle opening 44. The transparent cover 92 is at a distance of 0.2-1.0 mm above the upper surface 34 of the receptacle bottom 32. The transparent cover 92 is secured in place with the cover holder 94 using screws 100 into screw holes 110 of the receptacle body 42. A lower surface 112 of the cover holder 94 includes an O-ring groove 114, as shown in FIG. 1. FIG. 1 shows an O-ring 116 resting in the O-ring groove 114 of the cover holder 94 to provide a seal between the transparent cover 92 and the cover holder 94. FIG. 4 shows the top plate 90 which mounts on top of the housing 54 using screws 118 (shown in FIG. 5) and screw holes 120 of the housing 54 and the top plate 90. FIG. 4 shows an O-ring 122 laying on the housing 54 and an O-ring groove 124 in the top plate 90. The O-ring 122 rests in the O-ring groove 124 to provide a seal between the housing 54 and the top plate 90. The housing 54, top plate 90 and cover holder 94 are made of black plastic material, so as to be light absorbing and so as to be thermally insulating as compared to metal parts of the device 10. Nylon or ABS plastic may be used for the black plastic.

Figure 5:
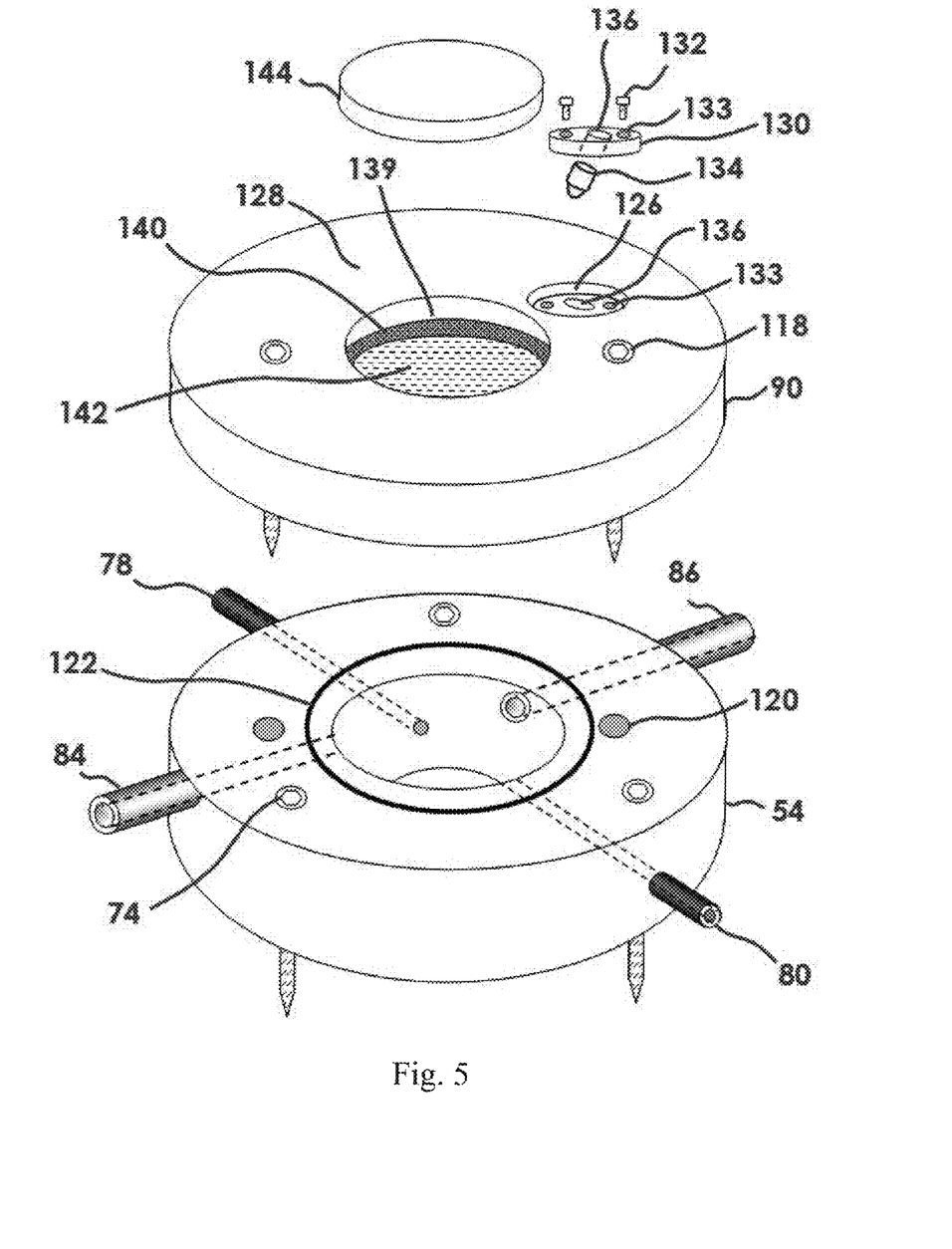
FIG. 5 is a perspective exploded view of components of the apparatus of FIG. 1 according to the present invention.

As shown in FIG. 5, the top plate 90 includes a recess 126 on a top side 128 which holds a light holder 130 by screws 132 using screw holes 133. The light holder 130 mounts a light emitting device shown as a light emitting diode 134 in a light opening 136. The light emitting diode 134 is high power and is of near infrared (NIR) or Infrared (IR) wavelength. FIG. 4 shows the diode 134 from a bottom side 138 of the top plate 90. The light opening 136 is at an angle of about 45° to direct a beam of light onto the mirrored upper surface 34. A light source with wavelength at between 840-1550 nm and radiant intensity of >250 mW/sr has been found to be suitable. Co-axially above the receptacle opening 44 in receptacle body 42 is a lens opening 139 to receive a lens holder 140 which secures a convex lens 142 in place. Secured above the lens 142 in the lens opening 138 is a digital image sensor 144. The lens 142 concentrates light received from the upper surface 34 onto the digital image sensor 144. With this arrangement a signal is produced as soon as light scattering occurs anywhere in the viewing chamber 88 below the lens 142. The image sensor 144 is connected to a data acquisition and monitoring computer (not shown). The image sensor is movable relative to the lens for adjusting the focus of light received from the sample onto the image sensor. Together, the above components form a receptacle that is a light excluding chamber.

As compared to prior art mechanized systems, the present invention has the following advantages. The present invention controls the sample thickness to no more than 1.0 mm, such that the opacity of the sample is sufficiently reduced. The present invention keeps the sample surface flat, such that the measurement is not affected by the change in meniscus with temperature. The present invention uses a light beam source of near infrared (NIR) or Infrared (IR) wavelength to allow light to penetrate the thin layer of transparent, translucent or opaque sample. The light beam source is located to direct a beam of light onto the surface at an incident angle so that light from the beam is reflected or absorbed by the surface. The present invention uses the light beam source of high power to provide more penetrating power through the thin layer of transparent, translucent or opaque sample. Together the viewing chamber and the components that make up the receptacle provide a light-proof and light-absorbing chamber and a liquid sample-receiving receptacle within the chamber having a bottom formed by a non-light-scattering surface.

A working model is envisioned to have the following attributes. The receptacle having a diameter of about 5 mm to 15 mm, so that only a small quantity of sample is required. The sample thickness is of about 0.2 mm to 1.0 mm. The removable transparent cover over the receptacle is made of glass. The upper surface of the receptacle bottom is preferably a smooth horizontal mirror surface for light reflection and signal amplification. The scattered light is measured at a location separated from the light beam reflected from the mirror surface so that the reflected beam does not interfere with scattered light measurements. Preferably, the incident angle between the light beam and the mirror surface is an acute angle of from 20° to 80°, and the scattered light is measured in a direction perpendicular to the surface. The light beam source is of near infrared (NIR) or infrared (IR) wavelength and high power, to assess the reduced opacity spectral region of the sample. The scattered light is detected by a ½ inches 3-megapixel CMOS digital image pixel sensor capable for near infrared and infrared signal detection, with sufficient pixel resolution to localize regions of light scattering and radiation when a light scattering phase is formed. A pixel map of 2048×1536 is found to be suitable.

Figure 6:
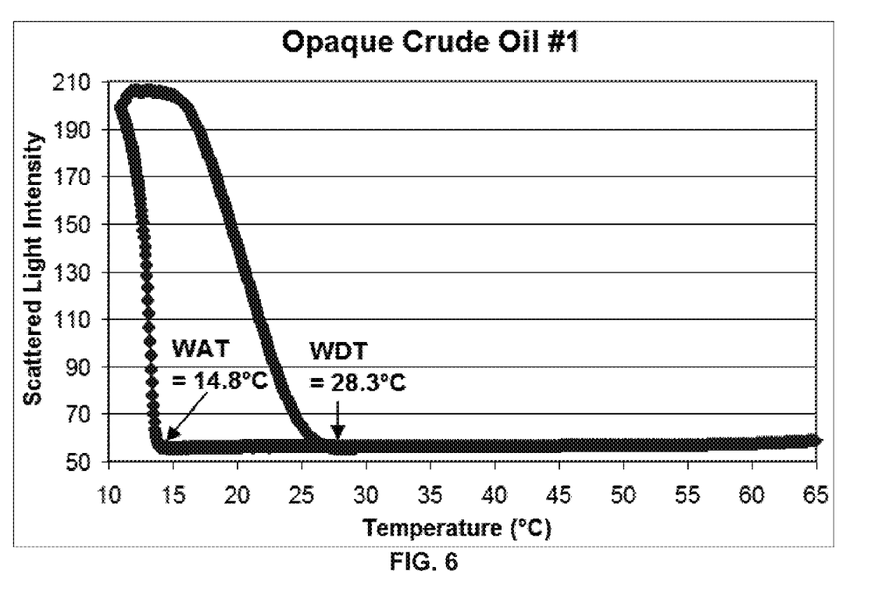
FIG. 6 is a graph of test results according to the present invention.

The method is the measurement of wax appearance temperature and wax disappearance temperature in a liquid using the above described embodiment. FIG. 6 shows results obtained in testing an opaque crude oil using wax appearance temperature measurement device. Prior to the test, the sample path should be clean and dry. The sample path includes the area between the upper surface 34 of the receptacle bottom 32 and the transparent cover 92, the paths along channels 76 inside the receptacle body 42, the sample inlet tube 78 and sample outlet tube 80. The whole sample path is kept at a temperature of at least 60° C. The sample is preheated in its original container at a temperature of at least 60° C. for 1 hour and loaded through the sample inlet tube 78 to fill the whole sample path. The viewing chamber 88 is then purged slowly with a dried gas that is inputted into the input tube 84 and released from the output tube 86 that are both connected to the purge ducts 82 for about two minutes. The viewing chamber 88 is then kept pressurized at a level of 1-2 psi with the dried gas. The temperature of the receptacle bottom 32 is lowered by the thermoelectric device 24 at a predetermined rate, such as 1.5±0.1° C./min, and the light beam source 134 is activated and the light beam is directed onto the mirrored surface of the upper surface 34. Prior to the formation of wax particles in the sample, the light beam is almost entirely reflected and only a small amount of scattered light is detected by the image sensor 144, which is shown as a generally horizontal line in FIG. 6. The horizontal line is a baseline. Once clouds of wax crystals start to form, the intensity of scattered light increases and FIG. 6 shows that the intensity starts to increases at 14.4° C., which is the wax appearance temperature (WAT) of the sample. After incurring sufficient waxes, the temperature of the receptacle bottom 32 is raised by the thermoelectric device 24 at a predetermined rate, such as 1.5±0.1° C./min. When the wax crystals start to melt, the scattered light intensity decreases, as FIG. 6 shows that the intensity returns to the baseline at 27.9° C., which is the wax disappearance temperature (WDT). At the end of the test, the thermoelectric device 24 warms the receptacle bottom 32 back to at least 60° C. and the device 10 is depressurized.

Figure 7:
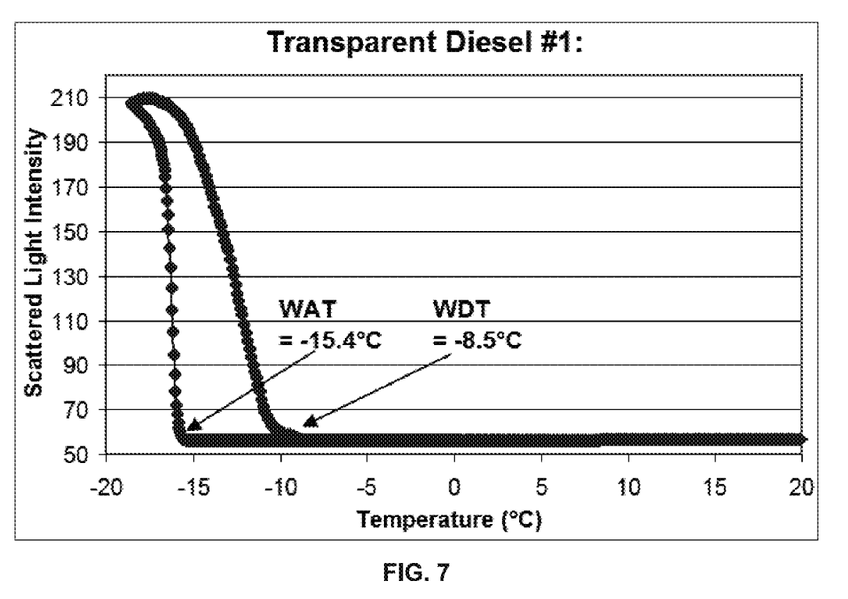
FIG. 7 is a graph of test results according to the present invention.
Figure 8:
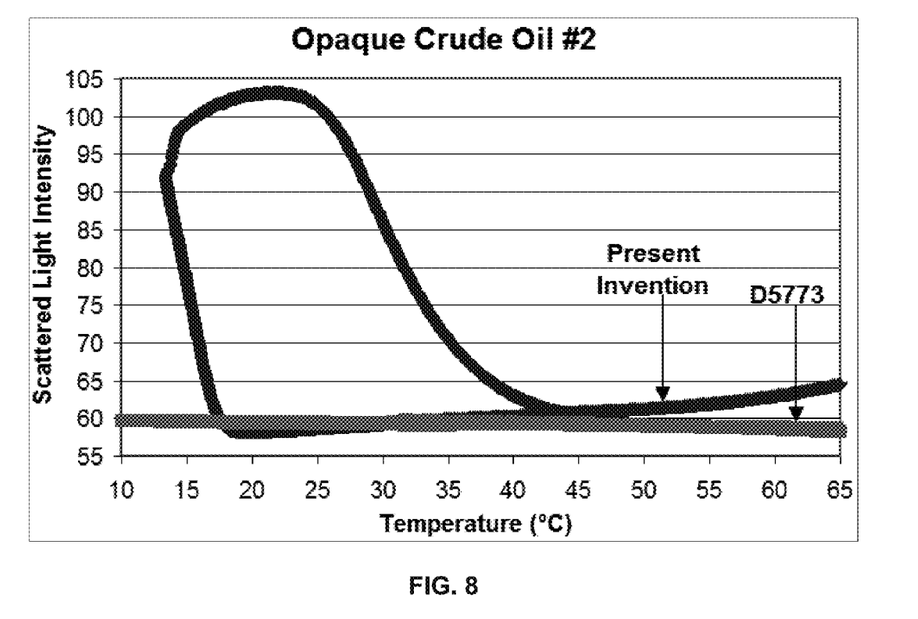
FIG. 8 is a graph of test results according to the present invention.
Figure 9:
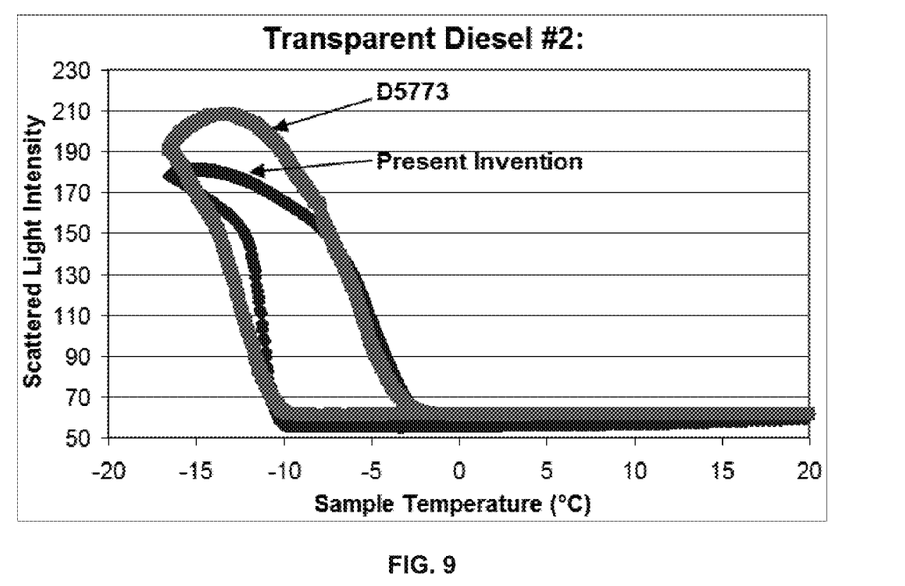
FIG. 9 is a graph of test results according to the present invention.

FIG. 7 shows results obtained in testing a transparent diesel in the device 10, which is sample DF2 1206 from the ASTM cross check program. The light intensity starts rising at the WAT of −15.4° C., which agrees well with the value published in the ASTM report (D2500 cloud point=−15.6° C.). The WDT is found to be at −8.5° C., when the light intensity returns to the baseline. FIG. 8 compares results obtained in testing another opaque crude oil using the device and using the ASTM D5773 method. No scattered light is detected by D5773 for this opaque sample, while high level of scattered light is detected with the device 10 of the present invention. The WAT and WDT are found to be at 18.7° C. and 46.2° C., respectively. FIG. 9 compares results obtained in testing another transparent diesel, using the device 10 and the ASTM D5773 method. Both methods can detect scattered light for this transparent sample. The WAT and WDT using both methods agree with one another and are found to be at −9.9° C. and −1.2° C., respectively. The method and the device 10 provide a flat sample surface to remove curvature of the meniscus and associated signal variation (a nuisance factor here). The method and device 10 also provide a sufficiently thin surface of liquid and a wavelength beyond the visible spectrum, which are necessary to reduce sample opacity.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

We claim:

1. An apparatus for detecting the temperature at which a transition occurs in a material sample between a non-light scattering liquid phase and a light scattering phase, comprising:
    a sample receptacle having a receptacle opening adapted to provide a sample area for receiving the sample for testing, said sample receptacle opening including a bottom, at least one side about said receptacle opening and an open top above said bottom and said at least one side, said at least one side about said receptacle opening being light absorbing, said bottom of said receptacle opening having an upper surface within said receptacle opening that has properties to reflect light;
    an inlet and an outlet connected to said receptacle opening adapted for sample insertion and removal;
    a transparent cover mounted over said open top of said receptacle opening to seal said receptacle opening between said bottom and said open top, said transparent cover adapted to allow light transmission;
    a thermo device adapted for heating and cooling of the sample contained in said receptacle opening;
    a thermometer adapted to register the current temperature of the sample in said receptacle opening;
    a viewing chamber above said transparent cover to view reflected light from said bottom of said receptacle opening, said viewing chamber surrounded by material that is light absorbing so as not to reflect light passing through said viewing chamber; and
    a light emitting device mounted to said apparatus to project light through said viewing chamber and said transparent cover such that said light enters said receptacle opening and reflects off said upper surface of said bottom of said receptacle opening.

2. The apparatus of claim 1, wherein a distance between said bottom of said receptacle opening and said open top at said transparent cover is not greater than 1.0 mm and is adapted to keep the sample flat such that the opacity of the sample is sufficiently reduced and meniscus effect is eliminated.

3. The apparatus of claim 1, further including a heat sink attached to said thermo device.

4. The apparatus of claim 1, wherein said thermo device is connected to said bottom of said receptacle opening in order to change the temperature of said bottom of said receptacle opening and wherein said bottom of said receptacle opening is made of a material having thermally-conductive properties.

5. The apparatus of claim 1, further including a lens co-axially above said receptacle opening to concentrate reflected light received said bottom of said receptacle opening.

6. The apparatus of claim 5, further including an image sensor to produce a signal change as light scattering intensity changes anywhere in said viewing chamber, said image sensor positioned above said lens, said lens positioned to concentrate reflected light received said bottom of said receptacle opening and direct reflected light at said image sensor to produce said signal change.

7. The apparatus of claim 5, wherein said lens is convex.

8. The apparatus of claim 1, further including an image sensor, said image sensor to produce a signal change as light scattering intensity changes anywhere in said viewing chamber.

9. The apparatus of claim 1, wherein said upper surface within said receptacle opening is a mirror surface.

10. The apparatus of claim 1, wherein said viewing chamber includes an inlet and outlet to allow for gas purging of the viewing chamber.

11. The apparatus of claim 1, wherein said light emitting device produces light having a wavelength between 840-1550 nm and a radiant intensity of greater than 250 mW/sr.

12. The apparatus of claim 1, wherein said light emitting device is positioned to direct said light to strike said upper surface of said bottom of said receptacle opening at an incident angle between 20° to 80° so that said light penetrates the sample.

13. A method for detecting a temperature at which a transition occurs in a material sample between a non-light scattering liquid phase and a light scattering phase, and capable of detecting wax appearance and disappearance temperatures of a transparent, translucent, or opaque light, comprising:

provi­ding a sample path in and out of a sample receptacle having a receptacle opening to receive the sample for testing, providing a reflective bottom surface in the receptacle opening to reflect light that enters the receptacle opening, providing sides of the receptacle opening that are light absorbing;

providing a transparent cover to seal an open top of the receptacle opening;

purging the sample path and the receptacle opening to clean and dry the sample path and the receptacle opening;

providing a viewing chamber above the transparent cover of the receptacle opening to view reflected light from a bottom of the receptacle opening, wherein the viewing chamber is surrounded by material that is light absorbing so as not to reflect light passing through the viewing chamber;

purging the viewing chamber with a dried gas;

inputting a sample through the sample path and filling the receptacle opening with the sample;

providing a thermo device for heating and cooling of the sample contained in the receptacle opening, a thermometer to register the current temperature of the sample in the receptacle opening, a light emitting device mounted to project light through the viewing chamber and the transparent cover such that the light enters the receptacle opening and reflects off the reflective bottom surface in the receptacle opening, and an image sensor that produces a signal change as light scattering intensity changes anywhere in said viewing chamber;

inputting light into the viewing chamber which travels to the reflective bottom surface in the receptacle opening;

changing the temperature of the sample using the thermo device; and detecting changes in intensity of scattering of light reflected from the reflective bottom surface in the receptacle opening using the image sensor to sense appearance and disappearance of wax particles to determine wax appearance and disappearance temperatures of the sample.

14. The method of claim 13, further including using a receptacle opening having a distance between the reflective bottom surface of the receptacle opening and the transparent cover not greater than 1.0 mm to keep the sample flat such that opacity of the sample is sufficiently reduced and meniscus effect is eliminated.

15. The method of claim 13, wherein inputting light into the viewing chamber is inputted at a wavelength between 840-1550 nm and a radiant intensity of greater than 250 mW/sr.

16. The method of claim 13, further including maintaining the sample path at a temperature of at least 60° C. and pre-heating the sample in its original container at a temperature of at least 60° C. for 1 hour prior to inputting the sample into the receptacle opening.

17. The method of claim 13, further including pressurizing the viewing chamber to a level of 1-2 psi with dried gas.

18. The method of claim 13, further including lowering the temperature of the sample to allow wax crystals to form, so that the intensity of scattered light increases to determine the wax appearance temperature of the sample.

19. The method of claim 13, further including raising the temperature of the sample to allow wax crystals melt so that the intensity of scattered light decreases to determine the wax disappearance temperature of the sample.

20. The method of claim 13, further including using a lens to concentrate the light reflected from the sample onto the image sensor.

21. The method of claim 13, further including using a data acquisition and monitoring computer determining the wax appearance and disappearance temperatures by analyzing the scattered light intensity data from the image sensor as a function of sample temperature.

* * * * *